United States Patent [19]

Green et al.

[11] Patent Number: 4,735,691

[45] Date of Patent: Apr. 5, 1988

[54] METHOD FOR OPERATING ELECTROCHEMICAL DETECTOR CELL

[75] Inventors: Norman Green, Phoenix; Charles H. Ward, II, Baltimore, both of Md.

[73] Assignee: Allied Corporation, Morristown, N.J.

[21] Appl. No.: 816,648

[22] Filed: Dec. 23, 1985

[51] Int. Cl.$^4$ ............................................. G01N 27/46
[52] U.S. Cl. .................................. 204/1 T; 204/402; 204/406; 204/415; 204/431
[58] Field of Search ............... 204/1 T, 402, 431, 432, 204/412, 406, 415

[56] References Cited

U.S. PATENT DOCUMENTS

| Re. 31,914 | 6/1985 | Oswin et al. | 204/432 |
| 4,166,775 | 9/1979 | Bruckenstein et al. | 204/1 K |
| 4,500,391 | 2/1985 | Schmidt et al. | 204/412 |
| 4,505,784 | 3/1985 | Mund et al. | 204/402 |
| 4,566,949 | 1/1986 | Berger | 204/402 |

FOREIGN PATENT DOCUMENTS 1531761 11/1978 United Kingdom ............... 204/402

Primary Examiner—T. Tung
Attorney, Agent, or Firm—Bruce L. Lamb; Robert M. Trepp

[57] ABSTRACT

The method of operating a two electrode electrochemical detector cell in which the cell is connected to an external current measurement circuit through a cyclically operated switch which alternately opens and closes the connection between the cell and the external circuit. The cell is operated without bias potential. The peak current obtained from the cell after closing the connection to the external circuit may be measured immediately without any delay for transient current to decay. Means are disclosed for automatically compensating for background current error in the cell current measurement.

4 Claims, 3 Drawing Sheets

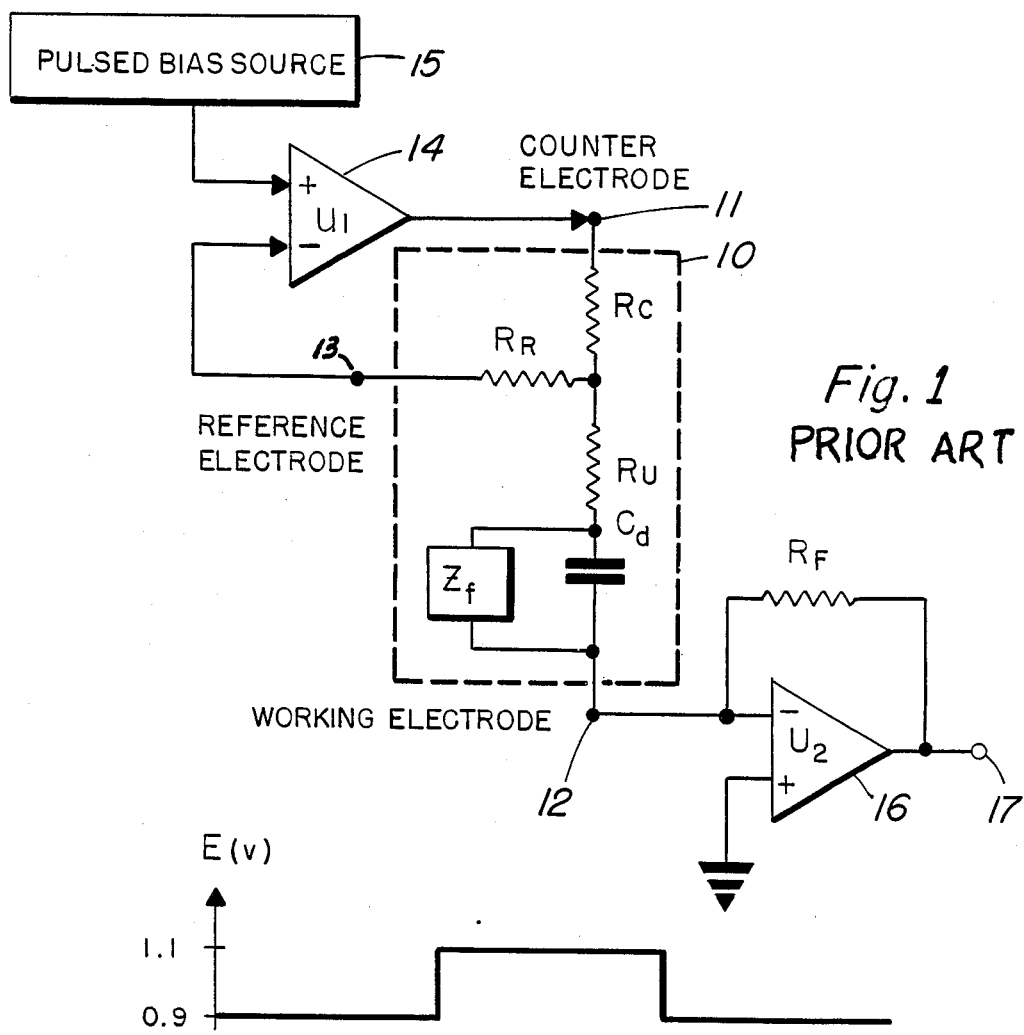
Fig. 1
PRIOR ART
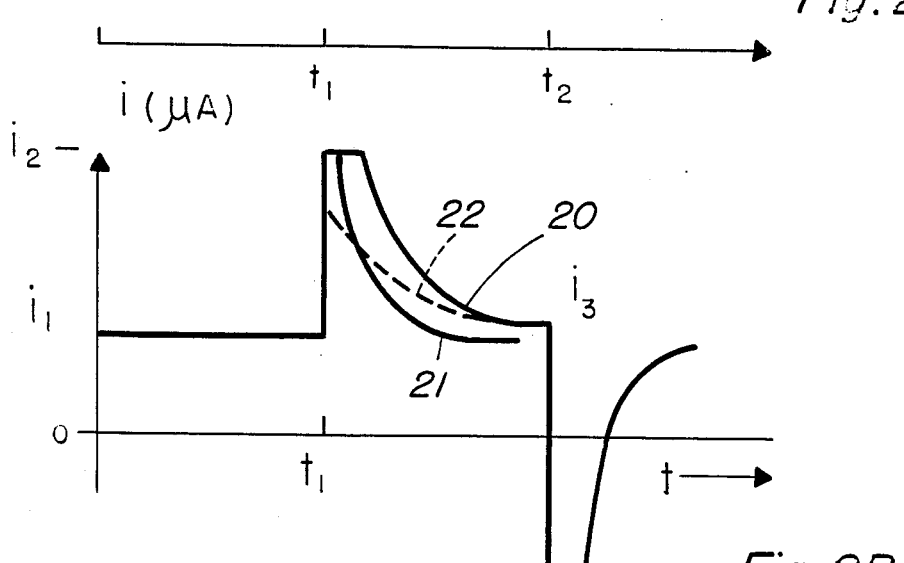
Fig. 2A
Fig. 2B

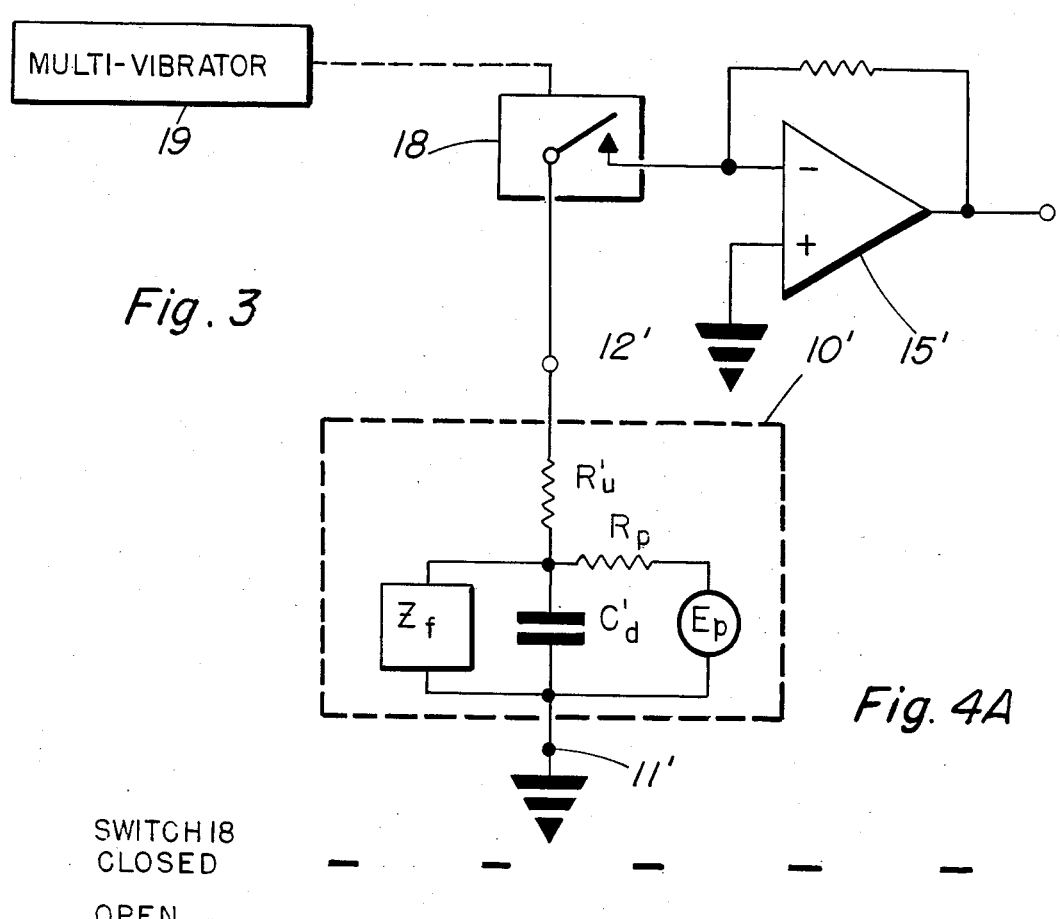
Fig. 3
Fig. 4A
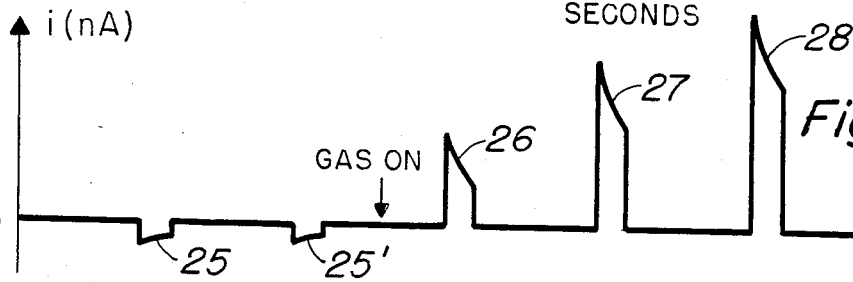
Fig. 4B
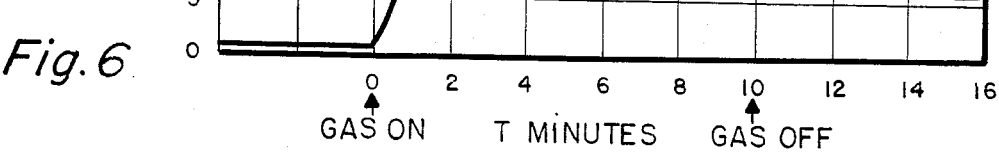
Fig. 6

METHOD FOR OPERATING ELECTROCHEMICAL DETECTOR CELL

The present invention relates generally to electrochemical cells for detecting the presence of noxious gases in the atmosphere and, in particular, to a method of operating such cells which provides both increased signal current output and improved signal current to background current ratio.

One form of electrochemical detector in prominent use is the differential pulse polarographic cell. This cell is of the three electrode type comprising a working electrode, a counter electrode, often referred to as an auxiliary electrode, and a reference electrode, all of which are immersed in an electrolyte. A potentiostat circuit, through the reference electrode, senses the relative potential at the working electrode and adjusts the potential applied to the cell between the counter electrode and the working electrode to conform to a particular analytical program.

In U.S. Pat. No. 4,500,391, issued Feb. 19, 1985 for "Method and System for Real Time Differential Pulse Detection", the potential at the working electrode is maintained at a bias level near to, but below that which would promote reaction between the analyte gas and the working electrode. Periodically, the bias is pulsed to the reactive level. The cell current is sampled at a time just prior to the beginning of a bias pulse and at a time just prior to the end of a bias pulse. The difference between these two current samples represents the signal current output of the cell. This method of operation tends to suppress the effect of background current in the current output of the cell.

In an example given in the referenced patent, if NO were to be detected, a fixed bias of 0.90 v. would be applied to the cell, which bias level is slightly below the redox potential of 1.0 v. of the species to be detected. Periodically, a pulse of 0.2 v. amplitude is superimposed on the fixed bias, raising the cell potential momentarily to 1.1 v. Prior to the appearance of a bias pulse, with the cell potential at 0.9 v., many of the common interferent gases, if present, will be reduced and result in a cell background current. After application of the bias pulse, the same background current will be included in the cell output current, along with any signal current due to the presence of analyte gas. By taking the difference between the amplitudes of a first cell current sample taken just prior to the appearance of a bias pulse and a second cell current sample taken just prior to the end of a bias pulse, a differential current sample is provided which should be indicative of the cell signal current alone.

Since the detector cell is electrically equivalent to a large value capacitor, any change in the value of the bias potential applied thereto results in the flow of a large value transient current, whether or not any analyte gas is present. It is necessary, therefore, to delay taking the second cell current sample until nearly the end of the bias pulse at a time when the transient charging current of the cell has decayed nearly to zero, otherwise the cell signal current is completely masked by the transient current.

It is known that when the external circuit of a detector cell remains open for a relatively extended time, so that no current can flow through the cell, and assuming analyte gas to be present, upon closing the external circuit a surge of current is observed which is from five to seven times greater than the steady state value of current flow. This initial surge of cell current is believed to be due to an initially high concentration gradient of the analyte gas at the working electrode of the cell when no current is flowing through the cell. Upon closing the cell circuit, the concentration gradient and the cell current diminish with time until steady state values are reached.

The method of operation of the detector cell set forth in the referenced patent inherently fails to take advantage of the high sensitivity which can be obtained through the increased concentration gradient effect. The fundamental disadvantage of prior pulse voltammetry methods lies in the necessity to delay sampling the cell output current until such time as the transient capacitive charging current therein has decayed nearly to zero. After such a delay, the cell signal will normally have diminished to a steady state value and the surge which occurs therein upon initially closing the cell external circuit becomes unobservable.

It is an object of the present invention to provide a method and means for operating an electrochemical gas detector cell which produces increased signal current from the cell.

It is another object of the invention to provide a method and means for compensating for background current in an electrochemical cell, whereby the ratio of signal current to background current is increased.

BRIEF DESCRIPTION

Briefly, the invention comprises the method of operating an electrochemical detector cell wherein no bias pulse is applied to the cell and the external circuit between the cell working electrode and counter electrode is open circuited for a first extended interval. Then the external circuit is closed through a low impedance current measurement circuit for a second interval preferably of shorter duration than the first interval. The opening and closing of the external circuit proceeds continuously in a regular cyclic manner. The current measurement circuit preferably includes an operational amplifier connected as a current to voltage converter, the output of which is supplied to a threshold detector and alarm or to a recorder. The electrochemical cell suitably comprises two electrodes, i.e. a working electrode and a counter electrode, of the same material immersed in an electrolyte. The need for cell bias is eliminated by so selecting the cell electrode and materials that oxidation or reduction of the species of interest occurs at the working electrode at zero relative potential. The working electrode is exposed to the airstream to be sampled through a permselective membrane which serves to filter out common interferent gases which may also react at zero relative potential.

Compensation for background current not caused by interferents is provided by supplying to the cell current the proper sense and magnitude to cancel the background current produced by the cell when exposed to clean air.

DESCRIPTION OF THE DRAWINGS

FIG. 1 is a simplified schematic diagram of a differential pulse polarographic detector cell of the prior art;

FIGS. 2A and 2B are waveform diagrams typifying the pulsed bias applied to the cell of FIG. 1 and the current output of the cell;

FIG. 3 is a simplified schematic diagram of a two electrode detector cell with means for operating the cell in accordance with the method of the invention;

FIGS. 4A and 4B are waveform diagrams showing the timing of the switch means of FIG. 3 and the current output of the cell of FIG. 3 prior to and after exposure of the cell to an analyte gas;

FIG. 6 is a chart showing the current output of the cell of FIG. 5 prior to and after exposure of the cell to a weak concentration of analyte gas.

DETAILED DESCRIPTION

Figure 5:
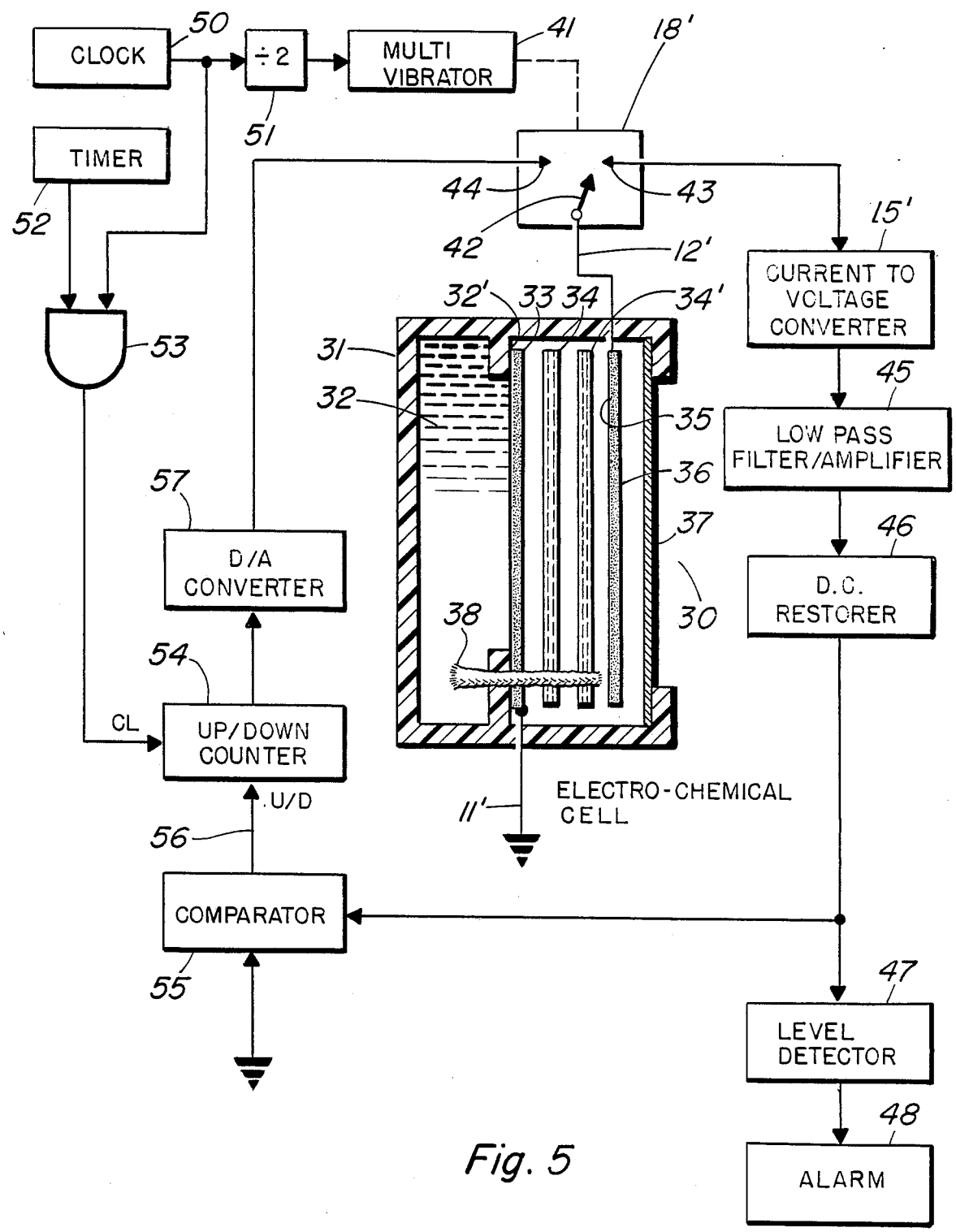
FIG. 5 is a functional block diagram, including a simplified cross section of a two electrode portable detector cell, showing the cell current measurement and automatic background current compensation circuits of the invention.

FIG. 1 is a simplified schematic diagram of the prior art differential pulse polarographic detector cell. the three electrode cell 10 thereof is represented by an equivalent electrical circuit in which the resistance through the electrolyte between the counter electrode terminal 11, the working electrode terminal 12 and the reference electrode terminal 13 are symbolized by a compensated resistor Rc, an uncompensated resistor Ru and a reference resistor Rr connected as shown. The double layer capacitances existing at the metal-electrolyte interface of the counter electrode and working electrode are shown as a single capacitor Cd, which is paralleled by a faradic impedance Zf. Impedance Zf may be regarded as a variable reistor having a value dependent upon the concentration of an analyte gas reacting at the working electrode.

An operational amplifier 14 receives an input bias potential function from a pulsed bias source 15 and operates as a potentiostat to maintain the potential at the junction of resistors Rc and Rr equal to the applied bias function. The working electrode terminal 12 of the cell is connected to the input of operational amplifier 16 serving as a current to voltage converter, such that the voltage $E_o$ at output terminal 17 is given by $E_o = i_c R_f$, where $i_c$ is the cell current.

FIGS. 2A and 2B are waveform diagrams typifying a pulsed bias input function to amplifier 14 and the resultant output of amplifier 15, scaled in terms of cell current, for the cell shown in FIG. 1. FIG. 2A illustrates an input bias function which might comprise, if NO is to be detected, a pulse of 0.2 v. amplitude superimposed upon a fixed bias level of 0.9 v. The pulse duration is 200 ms and the pulse repetition rate is 1 p.p.s. Line 20 of FIG. 2B is examplary of the waveform of the output of amplifier 15. Prior to the appearance of the leading edge of the bias pulse at time $t_1$, a background current $i_1$ flows through the cell having a magnitude dependent upon the concentration of interferent gases which are reactive at 0.9 v. At time $t_1$ the bias pulse causes a sharp increase in cell current to the saturation level $i_2$ of amplifier 15. Between time $t_1$ and time $t_2$ the cell bias remains constant at 1.1 v. and the cell current decays to a steady state level $i_3$. At the end of the bias pulse at time $t_2$, the reduction in cell bias drives amplifier 15 to its negative saturation level and thereafter the amplifier output gradually returns to the background current level $i_1$.

Waveform 20 is composed of two components shown by solid line 21 and dashed line 22. Line 21 has the larger peak value and is attributable to the current necessary to charge capacitor Cd through resistor Ru from a voltage level of 0.9 v. to 1.1 v. Line 22 has the smaller peak value and is attributable to the faradic current caused by the reaction of the analyte gas at the cell working electrode. The faradic current 22 is the data of interest but it is not separable from the charging current 21 in the output waveform 20. Consequently, it is necessary to delay sampling waveform 20 until very nearly time $t_2$, at which time the charging current 21 will have decayed to a negligible value. Near time $t_2$, however, the faradic current has diminished to a fraction of its initial value. Substantial improvement in sensitivity of the detector could be gained by the elimination of the charging current 21 from waveform 20, since the cell current could then be sampled much closer to time $t_1$ when the faradic current is near peak value.

FIG. 3 is a simplified schematic of a two electrode detector cell operated in accordance with the method of the invention. Cell 10' is represented by an equivalent circuit comprising resistor Ru', capacitor Cd', faradic impedance Zf, internal voltage source $E_p$ and resistor $R_p$. The working electrode of the cell is connected through terminal 12' and an electronic switch 18 to the input of a current to voltage converter 15'. The cell counter electrode is connected through terminal 11' to ground. Switch 18 is controlled by a multivibrator 18 to periodically open and close the connection between terminal 12' and the input to converter 15'.

The working electrode and the counter electrode are identical in form and material. Ideally, the internal voltage source $E_p$ and resistor $R_p$ are not present in the cell 10'. However, due perhaps to impurities in the electrode materials, small differences in electrode forms, impurities in the electrolyte, or other causes, a parasitic internal voltage source $E_p$ of about 1.5 mv. having a source resistance of about 2 megohms does manifest itself. This voltage source causes a cell background current of about 1 na. to appear when no reaction is taking place at the cell working electrode.

FIG. 4A is a timing diagram showing the operation of switch 18 (FIG. 3) and FIG. 4B is a waveform diagram typifying the output of converter 15' for several cycles before and after challenge of the cell by an analyte gas. In FIG. 4A, switch 18 is open for the interval $t_0-t_1$, closed for the interval $t_1-t_2$, again opened for $t_2-t_3$, again closed during $t_3-t_4$, etc. It should be noted that closure of switch 18 during times $t_1-t_2$, $t_3-t_4$, etc. merely completes the external circuit between cell terminals 11' and 12'. Switch closure does not vary the potential applied to the cell as in case of bias pulse $t_1-t_2$ of FIG. 2A.

Prior to application of a test analyte gas, during intervals $t_1-t_2$ and $t_3-t_4$, the cell output current (FIG. 4B) is only the low level background current 25, 25' generated by the cell internal voltage source $E_p$. This voltage may be either positive or negative, depending upon cell chemistry. Cell output current is zero at all times during which switch 18 is open.

After application of a test gas, between times $t_4$ and $t_5$, for switch closure intervals $t_5-t_6$, $t_7-t_8$ and $t_9-t_{10}$, the cell output, as shown in pulses 26, 27 and 28, rises abruptly from zero to a peak value then decays, following the same law as the faradic current 22 in FIG. 2B. The increase in the peak values of pulses 26, 27 and 28 results from increased diffusion with time of the test gas into the cell.

Since the whole of each of the current pulses 26, 27, 28 results from faradic current and no capacitive charging current is included therein, the peak value of each pulse is representative of the concentration of analyte gas and the output data is immediately useful after the beginning of a current pulse. Each output pulse is, however, affected by error due to background current of the magnitude of pulses 25, 25'. Means for compensating for such background current error are described in connection with FIG. 5.

FIG. 5 illustrates in block diagram and schematic form an electrochemical cell designed as a portable personal alarm for the detection of nerve gas, e.g. propoxy-(2)-methylphosphoryl fluoride. The electrochemical cell 30 generally follows the construction of the cell described in detail in the referenced U.S. Pat. No. 4,500,391. A molded plastic housing 31 defines an electrolyte reservoir 32 filled with an electrolyte, suitably a 60:40 solution of ethylene glycol:water containing an oxime in an alkaline buffer. The forward face of reservoir 32 is closed by a permeable membrane 32' which supports on the forward surface thereof the cell counter electrode 33 formed by vacuum deposition of a thin layer of silver. Two hydrophilic separators 34, 34' are interleaved between the counter electrode 33 and the cell working electrode 35. Electrode 35 is formed on the rear surface of a permeable membrane support 36 but is otherwise identical to electrode 33. The forward surface of membrane 36 is covered by a permselective membrane 37 which serves to filter interferent gases from the gases entering the cell. Membrane 37 may suitably comprise a 25 micron thick layer of microporous polyethylene impregnated with dimethylsilicone.

Separators 34, 34' are formed of layers of Whatman filter paper which are maintained saturated with electrolyte by a wick 38 communicating between the separators and reservoir 32. The planar parts of cell 30 are shown with substantial spacings therebetween for clarity of illustration. In actuality, these parts are assembled in close contacting relationship, with membranes 32 and 36 providing an effective fluid seal to prevent loss of electrolyte, while still permitting entry and diffusion of gases through the cell.

A conductive lead 12' extends from the working electrode 35 to an electronic switch 18', shown symbolically as a single pole-double throw switch. Counter electrode 38 is connected through lead 11' to circuit ground. Switch 18' is controlled by a multivibrator 41 so that switch arm 42 cycles between contacts 43 and 44 at the rate of approximately 0.5 Hz. Typically, the dwell of the switch arm on contact 43 is 0.4 sec. and on contact 44 is 1.6 sec. Switch arm 42 in contact with contact 43 is equivalent to the closed position of switch 18 in FIGS. 3 and 4A. In this position, working electrode 35 is connected to the low impedance input of a current to voltage converter 15', the output of which is highly amplified in a low pass filter-amplifier 45. Filter-amplifier 45 is designed to pass a band of frequencies extending between about 0.16 Hz. and 3 Hz., to suppress electrical noise, and includes several capacitively coupled amplifying stages. As a result of the capacitive coupling the unipolar signal at the input to amplifier 45 is converted to a bipolar signal at the output. Amplifier 45 is therefore followed by a d.c. restorer circuit 46 to restore unipolar characteristics to the amplified signal. The output of d.c. restorer 46 is compared with a fixed threshold voltage in a level detector 47 which activates an audible or visible alarm 48 whenever the signal output of d.c. restorer 46 exceeds the fixed threshold levels.

In one embodiment of the invention the current to voltage converter 15' transfer function was one nanoampere equals one microvolt. The overall voltage gain of filter amplifier 45 and d.c. restorer 46 was approximately 4000 and the threshold voltage was set at 12.5 mv. A cell output current of approximately 3 na. was therefore required to trigger the alarm.

As previously stated with reference to FIG. 4B, the signal current pulses 26, 27, 28 shown therein are in error by an amount equal to the background current pulses 25, 25'. Compensation for such background current is provided by the circuit elements next to be described.

A master clock 50 provides short duration clock pulses at the rate of 1.0 Hz. The clock pulses are divided by two in a divider 51 to provide trigger pulses to multivibrator 41 at the rate of 0.5 Hz. When power is first applied to the electronic components of the detector, a timer 52 is started. Timer 52 runs for eight minutes and then times out. While timer 52 is running, an output is provided which enables AND gate 53. While enabled, gate 53 passes clock pulses to the clock input of an up-down counter 54. Counter 54 may suitably have a capacity of eight bits and is preset to binary 1000 0000 at start-up. Cell 30 is assumed to be exposed only to clean air when first put into operation. At that time any output from d.c. restorer 46 is deemed to be due to background current. The output of d.c. restorer 46 is compared with zero (ground potential) in a comparator 55 which produces a binary output 1 or 0, depending on whether the output of d.c. restorer 46 is positive or negative. Binary 1 on counter input 56 steers the counter to count up one bit from the preset number for each clock pulse passed by gate 53. Binary 0 on counter input 56 steers the counter in the opposite direction.

The digital output of counter 54 is converted to an analog voltage in D/A converter 57. D/A converter produces 0 mv. output for binary 1000 0000, +350 mv. for binary 0000 0000 and −350 mv. for binary 1111 1111. The converter output voltage is supplied through a one megohm resistor (not shown) to contact 44 of switch 18' so that converter 57 is capable of sourcing a maximum of ±350 na. to cell 30.

The compensating circuit just described, including comparator 55, counter 54 and converter 57, is designed to automatically establish a compensating current of equal magnitude but opposite polarity to the background current of cell 30. This compensating current is furnished to the cell during the time switch arm 42 is in contact with contact 44 and, in effect, charges capacitor $C_d'$ (FIG. 3) to a potential equal and opposite to that of voltage source $E_p$. Upon engagement of switch arm 42 with contact 43, no current will flow from cell 30 due to background current. Any current flow then will be the result of faradic current, the magnitude of which will not be affected by background current error.

The automatic operation of the background current compensation means is best explained by a specific example. Suppose at the outset, cell 30 produces a background current of +20 na. into current to voltage converter 15' when switch arm 42 engages contact 43. This background current will appear at the output of d.c. restorer 46 as a positive voltage, causing the output of comparator 55 to be a binary 1. Counter 54 is accordingly steered to count up. During the first cycle of switch 18', two clock bits will pass gate 53 and advance the count of counter 54 from 1000 0000 to 1000 0010.

Converter 57 produces 0 ua. output for binary input 1000 0000 and −350 na. output for binary input 1111 1111. Therefore, each bit change in the binary input to the converter changes the output by $350/127 \approx 2.76$ na.

At the end of the first cycle of switch 18' a compensating current of about −5.5 na. is applied to the cell through contact 44 to reduce the background current by that amount. After four cycles of switch 18' the compensating current will have increased to about −22 na. resulting in a net current from the cell of approximately −2 na. at the beginning of the fifth cycle of switch 18'. In the fifth switch cycle the polarity of the output of d.c. restorer is negative, producing binary 0 at the output of comparator 55 and steering counter 54 to count down. The output of converter 57 at the end of the fifth switch cycle will therefore be reduced to about 17.5 na. In succeeding switch cycles the polarity of the output of d.c. restorer will alternate between positive and negative and the net current output of the cell during engagement of switch arm 42 with contact 43 will differ from zero by a maximum amount of ±1 bit (±2.76 na.) due to quantization error. After timer 52 times out, gate 53 is inhibited. No further clock pulses are passed to counter 54 and the counter output and converter output remain fixed at the values then pertaining.

FIG. 6 is a chart showing the response of one embodiment of the invention upon exposure to a weak concentration of nerve gas in air. The continuous line shown is actually the locus of a plurality of discrete peak values of cell output current measurements made at two second intervals.

At power up, sometime prior to time $T_o$, the cell background current has been reduced substantially to zero by the automatic background current compensation means. At time $T_o$ the detector is challenged by a concentration of 0.05 ug./l of nerve gas in air. After about 30 seconds the cell output has risen to about 3 na., sufficient to trigger the alarm. The relatively long times required for the cell output to approach equilibrium and to recover to zero output after removal of the challenge gas are thought to be due mainly to adsorption and desorption of the gas on the surfaces of the cell housing.

The invention claimed is:

1. The method of operating an electrochemical cell to provide improved sensitivity of said cell for the detection of the presence of particular species of gases in a mixture of gases, said cell having a working electrode, a counter electrode, an electrolyte in which said electrodes are immersed, there being zero relative potential applied between said working electrode and said counter electrode to promote reaction of gases within said cell, said working electrode being exposed to said mixture of gases, and means for electrically connecting each of said electrodes to an external electrical circuit, said external circuit including current measuring means, said species of gases to be detected being those gases which will react at said working electrode to produce current flow in said external circuit at zero relative potential applied between said working electrode and said counter electrode, comprising the steps of opening said external circuit for a first period of time to prevent current flow therethrough from said cell;

closing said external circuit for a second period of time to permit current flow therethrough from said cell;

measuring the current flow throough said external circuit immediately upon closing said external circuit; and repeating said steps of opening, closing and measuring in a continuous repetitive cyclic manner.

2. A method as claimed in claim 1 wherein said first period of time is of longer duration than said second period of time.

3. A method as claimed in claim 1 with the additional step of filtering said mixture of gases prior to exposure of said mixture to said working electrode of said cell to remove interferent gases from said mixture exposed to said electrode.

4. A method as claimed in claim 1 with the additional steps of:

exposing said cell working electrode to a clean mixture of gases which does not include any gases of the species to be detected;

measuring during repetitive ones of said second periods any current flow from said cell while exposed to said clean mixture;

after said measurement of said cell current while exposed to said clean mixture, supplying to said cell during repetitive ones of said first periods current of sufficient magnitude and proper polarity to neutralize said current measured during exposure of said cell to said clean mixture while thereafter exposing said cell to gas mixtures possibly containing the species of gases to be detected.

* * * * *